US012609189B2

(12) United States Patent
Jiang et al.

(10) Patent No.: US 12,609,189 B2
(45) Date of Patent: Apr. 21, 2026

(54) CARE PLAN RECOMMENDATION SYSTEM AND CARE PLAN RECOMMENDATION METHOD

(71) Applicant: Industrial Technology Research Institute, Hsinchu (TW)

(72) Inventors: Yue-Min Jiang, Hsinchu (TW);
Jian-Ren Chen, Hsinchu County (TW);
Ho-Hsin Lee, Hsinchu (TW);
Chun-Hao Hung, Taoyuan (TW)

(73) Assignee: Industrial Technology Research Institute, Hsinchu (TW)

( * ) Notice: Subject to any disclaimer, the term of this patent is extended or adjusted under 35 U.S.C. 154(b) by 317 days.

(21) Appl. No.: 18/393,708

(22) Filed: Dec. 22, 2023

(65) Prior Publication Data

US 2025/0210167 A1 Jun. 26, 2025

(51) Int. Cl.
*G06K 9/00* (2022.01)
*G06T 7/00* (2017.01)
(Continued)

(52) U.S. Cl.
CPC ........... *G16H 20/00* (2018.01); *G06T 7/0012* (2013.01); *G16H 50/20* (2018.01); *G16H 50/70* (2018.01);
(Continued)

(58) Field of Classification Search
CPC ........ G16H 20/00; G16H 50/20; G16H 50/70; G16H 70/20; G16H 30/40; G16H 10/60;
(Continued)

(56) References Cited

U.S. PATENT DOCUMENTS 11,045,271 B1 6/2021 Tran
2010/0314936 A1 12/2010 Benedict et al.
(Continued)

FOREIGN PATENT DOCUMENTS

CN 113168921 7/2021
CN 114661995 6/2022
(Continued)

OTHER PUBLICATIONS

Rayner, Robyn, et al. "The STAR classification: Utility for determining healing times and dressing costs associated with skin tear management." Wound Practice & Research: Journal of the Australian Wound Management Association 29.4 (2021): 190-197. (Year: 2021).*
(Continued)

*Primary Examiner* — Gregory A Morse
*Assistant Examiner* — Owais Iqbal Memon
(74) *Attorney, Agent, or Firm* — JCIPRNET

(57) ABSTRACT

A care plan recommendation method includes: capturing a wound image of a wound; analyzing a wound status of the wound based on the wound image; filtering out similar case data from wound case data based on at least one filtering condition according to the wound status; summarizing into dressing types according to a part of the similar case data in the similar case data; calculating average recovery days, average recovery cost and recovery cost standard deviation corresponding to at least one dressing item in each dressing type according to at least part of the similar case data associated with each of the dressing types, and generating and displaying a dressing usage result; searching for keywords from the at least part of the similar case data associated with each dressing type, and converting the keywords to generate and display a care method text and a life note text through GPT.

12 Claims, 9 Drawing Sheets

(51) Int. Cl.
 *G16H 20/00* (2018.01)
 *G16H 50/20* (2018.01)
 *G16H 50/70* (2018.01)
 *G16H 70/20* (2018.01)
(52) U.S. Cl.
 CPC ... *G16H 70/20* (2018.01); *G06T 2207/30088*
 (2013.01)
(58) Field of Classification Search
 CPC ........ G16H 40/20; G16H 40/67; G16H 50/30;
 G16H 40/63; G16H 15/00; G16H 80/00;
 G16H 30/20; G06T 7/0012; G06T
 2207/30088
 See application file for complete search history.

(56) References Cited

U.S. PATENT DOCUMENTS

| | | | |
|---|---|---|---|
| 2021/0142890 A1 | 5/2021 | Adiri et al. | |
| 2021/0290152 A1* | 9/2021 | Vogel ..................... | G16H 40/67 |
| 2021/0353213 A1* | 11/2021 | Heneghan ............ | A61B 5/4848 |

FOREIGN PATENT DOCUMENTS

| | | |
|---|---|---|
| TW | 201137634 | 11/2011 |
| TW | 201802761 | 1/2018 |
| TW | I689945 | 4/2020 |
| TW | I726268 | 5/2021 |
| TW | I801311 | 5/2023 |

OTHER PUBLICATIONS

"Office Action of Taiwan Counterpart Application", issued on Sep. 20, 2024, p. 1-p. 3.

* cited by examiner

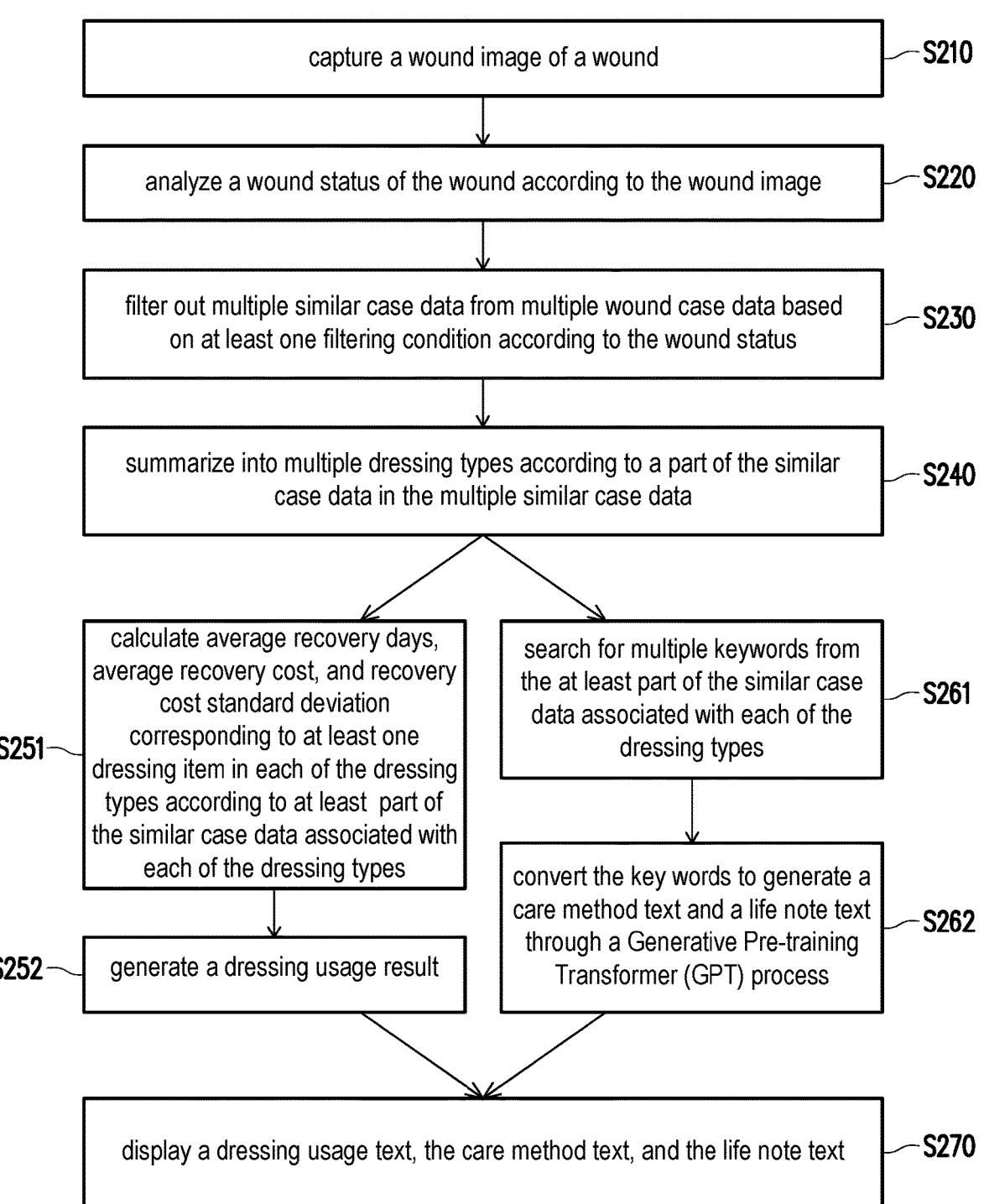

capture a wound image of a wound —S210 analyze a wound status of the wound according to the wound image —S220 filter out multiple similar case data from multiple wound case data based on at least one filtering condition according to the wound status —S230 summarize into multiple dressing types according to a part of the similar case data in the multiple similar case data —S240

S251— calculate average recovery days, average recovery cost, and recovery cost standard deviation corresponding to at least one dressing item in each of the dressing types according to at least part of the similar case data associated with each of the dressing types search for multiple keywords from the at least part of the similar case data associated with each of the dressing types —S261

S252— generate a dressing usage result convert the key words to generate a care method text and a life note text through a Generative Pre-training Transformer (GPT) process —S262 display a dressing usage text, the care method text, and the life note text —S270

| case number | condition 1 | condition 2 | condition 3 | condition 4 | condition 5 | ... | condition N-1 | condition N |
|---|---|---|---|---|---|---|---|---|
| 001 | 0 | 1 | 0 | 1 | 0 | ... | 0 | 0 |
| 002 | 0 | 0 | 0 | 0 | 0 | ... | 1 | 0 |
| 003 | 1 | 1 | 1 | 1 | 1 | ... | 1 | 1 |
| 004 | 1 | 0 | 0 | 0 | 0 | ... | 1 | 0 |
| 005 | 0 | 0 | 0 | 0 | 0 | ... | 1 | 0 |
| 006 | 1 | 1 | 1 | 1 | 1 | ... | 0 | 0 |
| 007 | 1 | 0 | 1 | 1 | 0 | ... | 1 | 0 |
| 008 | 0 | 1 | 1 | 0 | 0 | ... | 1 | 1 |
| 009 | 0 | 1 | 0 | 0 | 0 | ... | 0 | 1 |
| 010 | 0 | 0 | 0 | 0 | 0 | ... | 1 | 0 |
| 012 | 0 | 1 | 0 | 0 | 0 | ... | 1 | 0 |
| 013 | 0 | 0 | 0 | 0 | 0 | ... | 1 | 0 |
| . | . | . | . | . | . | | . | . |

FIG. 3C

CARE PLAN RECOMMENDATION SYSTEM AND CARE PLAN RECOMMENDATION METHOD

TECHNICAL FIELD

The disclosure relates to a recommendation technology, and in particular to a care plan recommendation system and a care plan recommendation method.

BACKGROUND

Approximately 3 to 6 million people in the United States suffer from non-healing wounds, resulting in significant health care expenditures with an estimated total cost of more than $3 billion per year. The prevalence rate of diabetes in Taiwan is 10.83%, and 15% of diabetic patients will develop chronic wounds, which not only heal slowly, but also often result in wound infection, fever, repeated medication, debridement surgery, and even life-threatening sepsis. Professional wound experts (wound nurses) can provide better care quality than ordinary nurses, and can accelerate the patient's wound healing time by 25 days or more than 2 times. Through the assistance of intelligent systems, wound care costs can be reduced by 1.38 billion pounds per year.

According to a survey by the US NIH (National Institutes of Health), the accurate wound care rate of general nursing personnel is only about 69%. In Taiwan, training as a wound expert requires 343 hours of training and 6 months of practical experience (>200,000 NTD). Only large-scale hospitals are willing to train wound experts. Only about 100 of the 68,000 nurses in Taiwan have obtained the WCET certificate, and even fewer have the ability to practice independently.

As the degree and time of wound healing vary, the environment required and the dressings provided will also vary. Proper use of appropriate dressings and frequency can effectively avoid re-injury to the wound caused by drug resistance or excessively frequent dressing changes.

Dressings are under demassification. Different types of wounds have corresponding special dressings, and the use of dressings varies according to the wound recovery stage, which is relatively complicated. For example, a certain manufacturer produces 3 types of dressings for caesarean sections, 6 types of dressings for chronic wounds, 6 types of dressings for breast postoperative wounds, and 4 types of dressings for minimally invasive postoperative wounds. The suitable dressings for each type of wounds are different. The wound experts may use at least 3,000 or more dressing items, and general caregivers may use more than 300 dressing items. In addition, the dressing name, the product name, the usage method, or the contraindications (the precautions) of the dressings are such large amount of information, which makes it impossible for caregivers to accurately implement care.

Furthermore, for elderly patients in rural areas, long-distance medical examinations are a huge burden. For example, patients with chronic pressure ulcers need to regularly return to the clinic for wound debridement care, be accompanied by family members, and make appointments for rehabilitation bus transportation. In addition to time (2-3 times/2 months) and cost, there are still many inconveniences. Moreover, the recovery rate of the wound healing process varies with the environment. Failure to effectively use the correct dressing prolongs the healing time, and increases the number of doctor visits and medical costs.

Therefore, how to apply a feature extraction technology of care records and dressing instructions, thereby generating a feature correlation between query case representations and dressings and the health education text, add search conditions to generate key features based on required efficacy, and make the recommendations for dressing product names, care methods, and treatment methods are issues to be solved in this field.

SUMMARY

The disclosure provides a care plan recommendation system, which includes a storage device, an image capturing device, a processor, and a display. The storage device is used to store multiple wound case data. The image capturing device is used to capture a wound image of a wound. The processor is coupled to the image capturing device and the storage device for executing: analyzing a wound status of the wound according to the wound image; filtering out multiple similar case data from the multiple wound case data based on at least one filtering condition according to the wound status; summarizing into multiple dressing types according to a part of the similar case data in the multiple similar case data; calculating average recovery days, average recovery cost, and recovery cost standard deviation corresponding to at least one dressing item in each of the dressing types according to at least part of the similar case data associated with each of the dressing types, and generating a dressing usage result; searching for multiple keywords from the at least part of the similar case data associated with each of the dressing types, and converting the keywords to generate a care method text and a life note text through a Generative Pre-training Transformer (GPT) process; and displaying the dressing usage result, the care method text, and the life note text. The display is coupled to the processor and used to display the dressing usage result, the care method text, and the life note text.

In an embodiment, the wound status includes a numerical record and a text record.

In an embodiment, the processor is further configured to convert the multiple wound case data into an intersection matrix based on the at least one filtering condition according to the wound status, filter out the multiple similar case data based on the intersection matrix, and generate a cost-effectiveness distribution diagram based on the multiple similar case data.

In an embodiment, the cost-effectiveness distribution diagram includes multiple display points, and each of the display points is associated with a current cost and a healing speed of each of the multiple similar case data.

In an embodiment, the processor is further configured to receive a selection command and a distribution command corresponding to one of the display points, and filter out the part of the similar case data based on the selection command and the distribution range command.

In an embodiment, the processor is further configured to search for the keywords according to a health education text in at least part of the similar case data associated with each of the dressing types.

The disclosure provides a care plan recommendation method, including: capturing the wound image of the wound; analyzing the wound status of the wound according to the wound image; filtering out the multiple similar case data from the multiple wound case data based on the at least one filtering condition according to the wound status; summarizing into the dressing types according to the part of the similar case data in the multiple similar case data; calculating the average recovery days, the average recovery cost, and the recovery cost standard deviation corresponding to the at least one dressing item in each of the dressing types according to the at least part of the similar case data associated with each of the dressing types, and generating the dressing usage result; searching for the keywords from the at least part of the similar case data associated with each of the dressing types, and converting the keywords to generate the care method text and the life note text through the GPT process; and displaying the dressing usage result, the care method text, and the life note text.

In an embodiment, the wound status includes the numerical record and the text record.

In an embodiment, the care plan recommendation method further includes: converting the multiple wound case data into the intersection matrix based on the at least one filtering condition according to the wound status, filtering out the multiple similar case data based on the intersection matrix, and generating the cost-effectiveness distribution diagram based on the multiple similar case data.

In an embodiment, the cost-effectiveness distribution diagram includes the display points, and each of the display points is associated with the current cost and the healing speed of each of the multiple similar case data.

In an embodiment, the care plan recommendation method further includes: receiving the selection command and the distribution range command corresponding to one of the display points, and filtering out the part of the similar case data based on the selection command and the distribution range command.

In an embodiment, the care plan recommendation method further includes: searching for the keywords according to the health education text in the at least part of the similar case data associated with each of the dressing types.

Based on the above, the care plan recommendation system and the care plan recommendation method of the disclosure apply a feature extraction technology of care records and dressing instructions, thereby generating a feature correlation between query case representations and dressings and the health education text. Search conditions are added to generate key features based on required efficacy, and the recommendations are made for dressing product names, care methods, and treatment methods.

BRIEF DESCRIPTION OF THE DRAWINGS

FIG. 2 is a flow chart of a care plan recommendation method according to an embodiment of the disclosure.

FIG. 3C is a schematic diagram of converting the multiple similar case data into an intersection matrix in a care plan recommendation method according to an embodiment of the disclosure.

DETAILED DESCRIPTION OF DISCLOSED EMBODIMENTS

Figure 1:
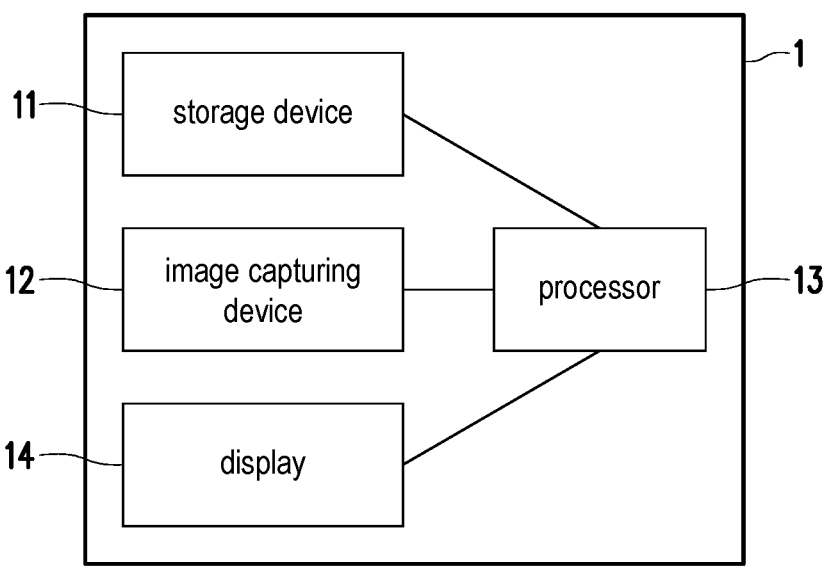
FIG. 1 is a structural diagram of a care plan recommendation system according to an embodiment of the disclosure.

Some embodiments of the disclosure will be described in detail below with reference to the accompanying drawings.

Reference numerals quoted in the following description will be regarded as the same or similar components when the same reference numerals appear in different drawings. The embodiments are merely a part of the disclosure and do not disclose all possible implementations of the disclosure.

FIG. 1 is a structural diagram of a care plan recommendation system 1 according to an embodiment of the disclosure. Referring to FIG. 1, the care plan recommendation system 1 includes a storage device 11, an image capturing device 12, a processor 13, and a display 14. The processor 13 is coupled to the storage device 11, the image capturing device 12, and the display 14. Practically speaking, the care plan recommendation system 1 may be implemented by a computer device, such as a desktop computer, a notebook computer, a tablet computer, a workstation, and other computer devices with computing functions, display functions, and networking functions. The disclosure is not limited thereto.

The storage device 11 is used to store multiple wound case data. Each of the wound case data at least includes a case number, patient information, a recording date, a wound image, a wound status, etc. The wound status in each of the wound case data may capture the wound image through a wound machine, and then perform an artificial intelligence automatic calculation on the wound image to automatically calculate a wound size, a wound tissue ratio, and other wound data through an application for the wound machine to act as a numerical record of the wound status in each of the wound case data. The wound size at least includes data such as a length, a width, a depth, and an area of the wound, while the wound tissue ratio at least includes data such as an epithelial ratio, a granulation ratio, a slough ratio, and a necrosis ratio of the wound. In addition, each of the wound case data further includes a text record to record the patient information of the wound case, wound information (such as a wound fluid volume, a wound fluid color), wound description (such as a wound shape), etc.

Practically speaking, the storage device 11 is, for example, a static random access memory (SRAM), dynamic random access memory (DRAM), other memories, or cloud storage space built into the desktop computer, the notebook computer, the tablet computer, or the workstation implementing the care plan recommendation system 1. The disclosure is not limited thereto.

The image capturing device 12 is used to capture the wound image of the wound. Practically speaking, the image capturing device 12 may be the image capturing device of the wound machine, an equipment with an image capturing function built in the desktop computer, the notebook computer, the tablet computer, and the workstation implementing the care plan recommendation system 1, or a camera, a video recorder, and other devices having the image capturing function and connected to the computer device in a wired or wireless manner implementing a care plan recommendation system 2. The disclosure is not limited thereto.

The processor 13 may be a central processing unit (CPU), a microprocessor, or an embedded controller built into the desktop computer, the notebook computer, the tablet computer, or the workstation implementing the care plan recommendation system 1. The display 14 may be a built-in display or an external display device of the desktop computer, the notebook computer, the tablet computer, or the workstation implementing the care plan recommendation system 1. The disclosure is not limited thereto.

The storage device 11, the image capturing device 12, the processor 13, and the display 14 in the care plan recommendation system 1 work together to execute a care plan recommendation method 2. FIG. 2 is a flow chart of the care plan recommendation method 2 according to an embodiment of the disclosure. The care plan recommendation method 2 in FIG. 2 may capture the wound image of the wound through the image capturing device 12 of the care plan recommendation system 1 in FIG. 1, and then read the wound case data and the wound image captured from the wound by the image capturing device 12 from the storage device 11 simultaneously through the processor 13. A dressing usage result, a care method text, and a life note text related to the wound are generated based on the multiple wound case data and the captured wound image. Finally, the dressing usage result, the care method text, and the life note text are displayed through the display 14. The care plan recommendation method 2 includes steps S210 to S240, S251 to S252, S261 to S262, and S270. Next, referring to FIG. 1 and FIG. 2 at the same time, the care plan recommended method 2 is described below.

In step S210, the wound image of the wound is captured by the image capturing device 12. As mentioned above, the wound image of the wound may be captured by the wound machine or the image capturing device, the equipment with the image capturing function built in the desktop computer, the notebook computer, the tablet computer, and the workstation implementing the care plan recommendation system 1, or the camera, the video recorder, and other equipment having the image capturing function and connected to the computer device in a wired or wireless manner implementing the care plan recommendation system 2.

In step S220, the wound status of the wound is analyzed by the processor 13 according to the wound image. Specifically, the application for the wound machine uses the processor 13 to automatically calculate outline and tissue of the wound on the wound image using the artificial intelligence, and analyze the wound status of the wound, including wound data such as the wound size and the wound tissue ratio.

In step S230, multiple similar case data are filtered out from the multiple wound case data in the storage device 11 by the processor 13 based on at least one filtering condition according to the wound status.

Figure 3A:
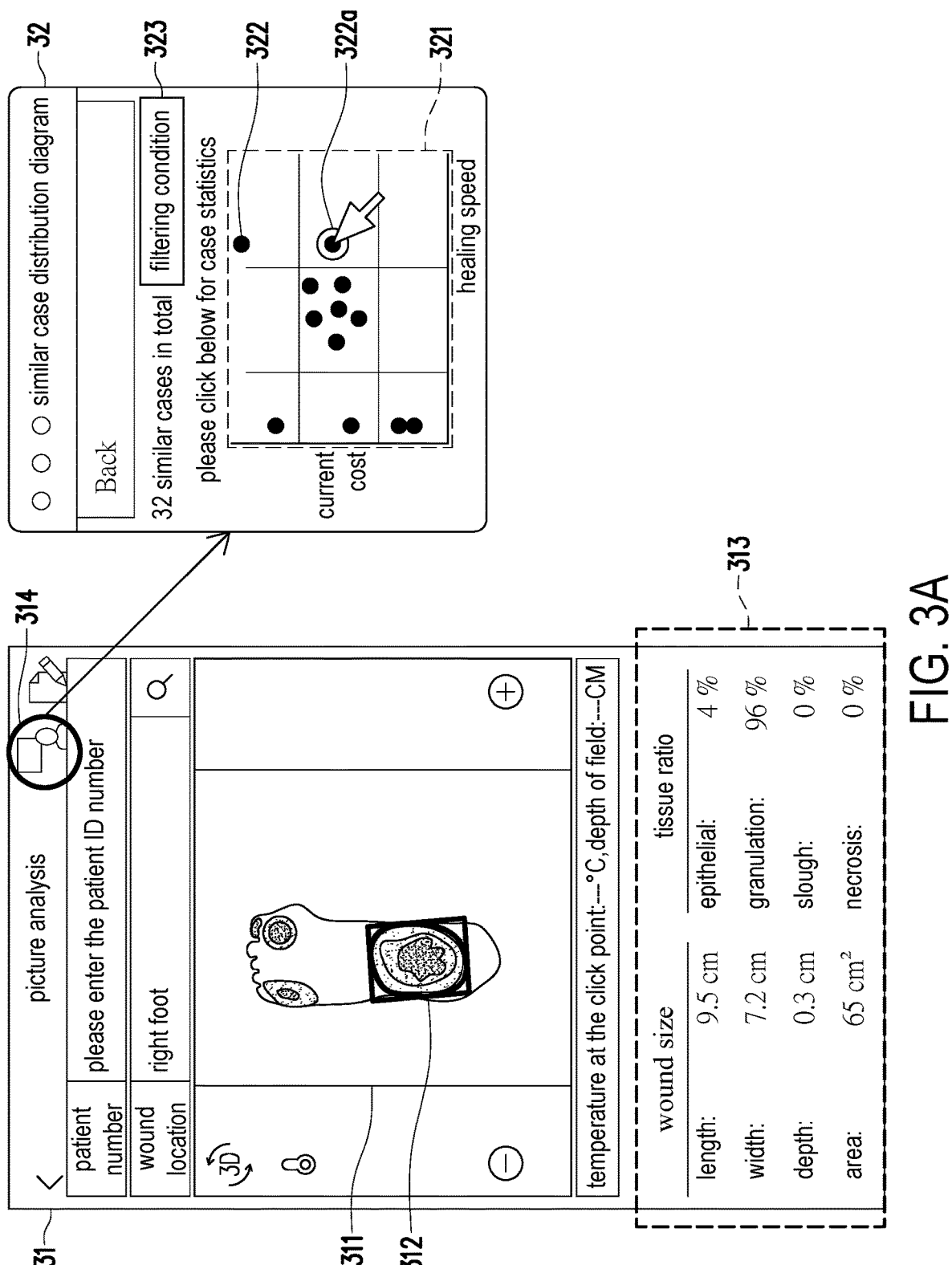
FIGS. 3A and 3B are schematic diagrams of filtering out multiple similar case data in a care plan recommendation method according to an embodiment of the disclosure.
Figure 3B:
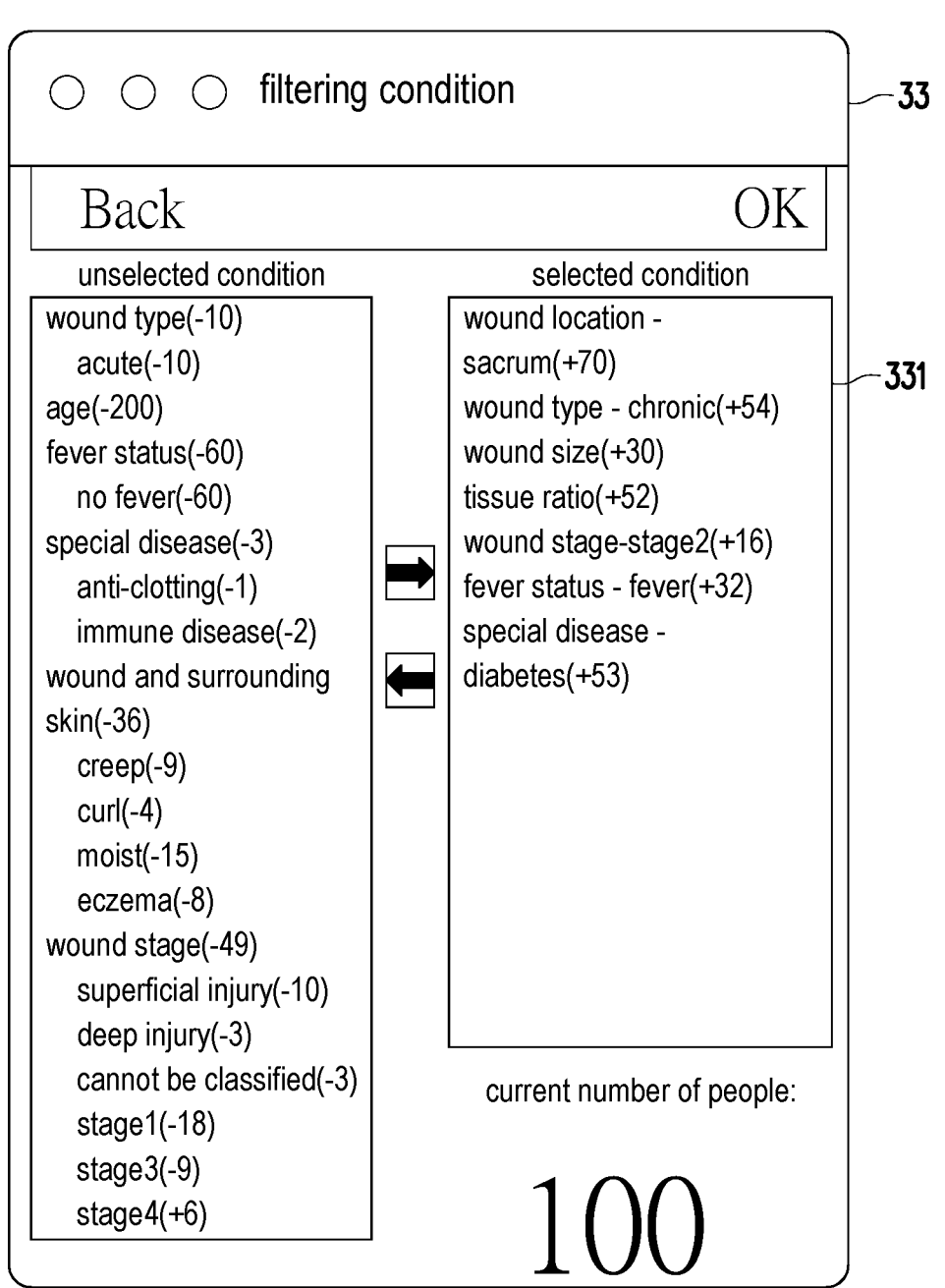

FIGS. 3A and 3B are schematic diagrams of filtering out multiple similar case data in a care plan recommendation method 2 according to an embodiment of the disclosure. Referring to FIG. 3A, a wound image 311 is displayed in an application 31. A user may click on a wound 312 which the user wants to analyse in the wound image 311, then a wound status 313 corresponding to the wound 312 may be displayed in the application 31.

Next, the user may click on a filtering button 314 in the application 31. The processor 13 filters out the multiple similar case data from the multiple wound case data in the storage device 11 according to the wound status 313, and the application 31 pops up a similar case distribution diagram 32. The similar case distribution diagram 32 shows how many similar case data there are, and the similar case data is presented in a form of a cost-effectiveness distribution diagram 321. There are multiple display points 322 in the cost-effectiveness distribution diagram 321. Each of the display points 322 is associated with a current cost and a healing speed of one similar case data.

The similar case distribution diagram 32 may also provide a target display point 322a and a filtering condition 323 for the user to click on to limit the wound case data to filter out the similar case data, thereby improving the effectiveness of a recommendation result. A patient record is used as a main filtering condition. There is a default set when the system is activated. After the user selects the condition, the new condition is directly mapped to an intersection matrix field sequence of the similar cases, thereby filtering out a case matching the condition. Finally, a 2D chart is used to present the increase or decrease in the number of recommended people for each condition.

There are many conditions to choose from in a filtering condition window 33 in FIG. 3B, such as: a wound type, a wound location, a wound type, a wound size, etc. The user may select a condition in the filtering condition window 33 for the type that the user wants to limit the wound case data according to the wound status, and place the condition in a selected condition box 331. The processor 13 filters out the multiple similar case data from the multiple wound case data according to the filtering condition in the selected condition box 331. The user may also adjust an importance priority of the filter condition in the selected condition box 331.

FIG. 3C is a schematic diagram of converting the multiple similar case data into an intersection matrix 34 in a care plan recommendation method 2 according to an embodiment of the disclosure. Referring to FIGS. 3A to 3C at the same time, when the user select the condition in the filtering condition window 33 for the type that the user wants to limit the wound case data according to the wound status, and place the condition in the selected condition bow 331, the processor 13 converts the multiple wound case data into the intersection matrix 34 according to the filtering condition in the selected condition box 331, and filters out the multiple similar case data based on the intersection matrix 34. The intersection matrix 34 includes the similar case data matching at least one filtering condition. Multiple conditions 341 (conditions 1 to N) in FIG. 3C are the filtering conditions in the selected condition box 331 and the cost-effectiveness distribution diagram is generated based on the multiple similar case data.

Referring to FIG. 2 again, in step S240, multiple dressing types are summarized by the processor 13 according to a part of the similar case data in the multiple similar case data.

Figure 4:
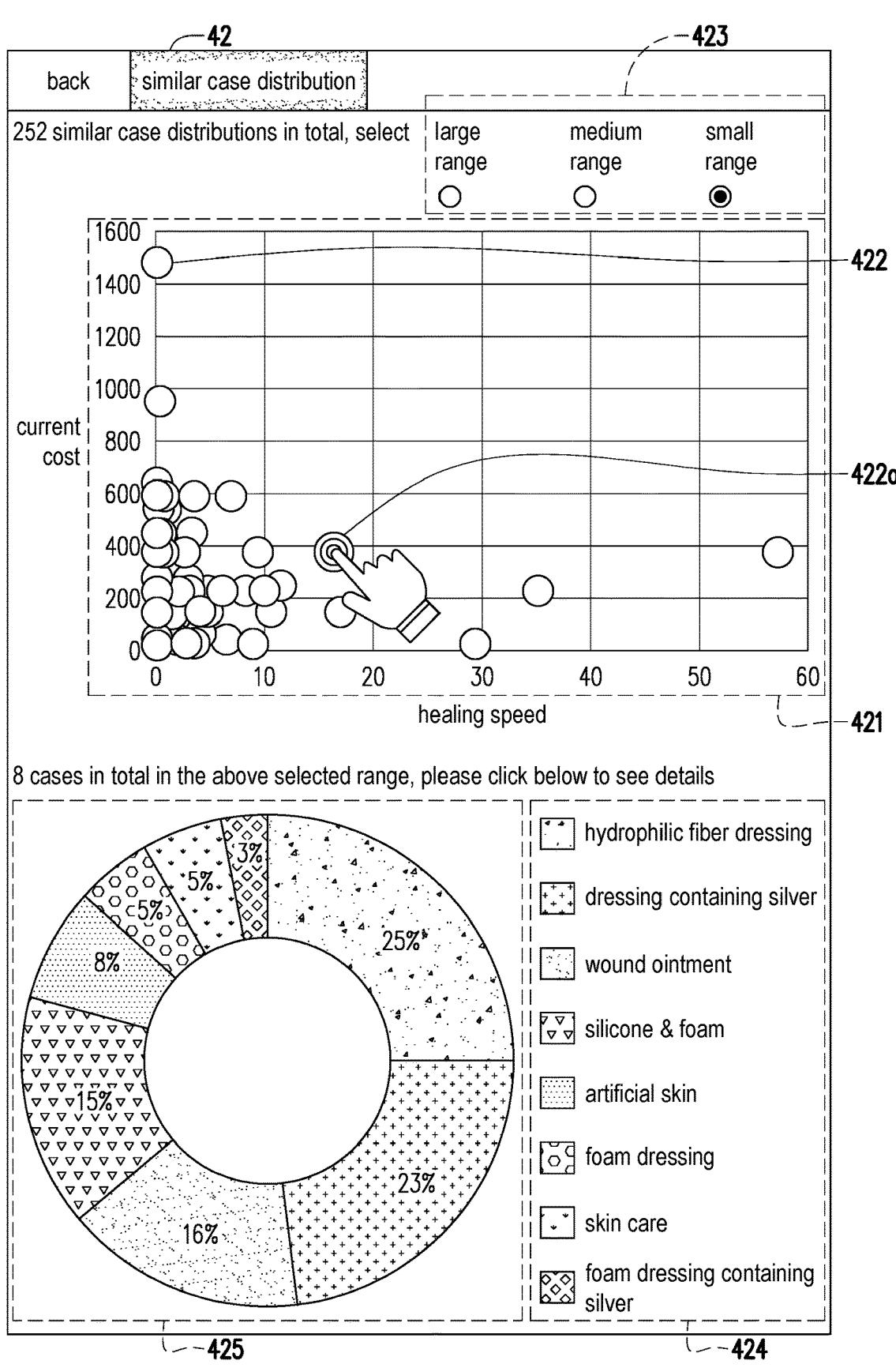
FIG. 4 is another schematic diagram of filtering out multiple similar case data in a care plan recommendation method 2 according to an embodiment of the disclosure.

FIG. 4 is another schematic diagram of filtering out multiple similar case data in a care plan recommendation method 2 according to an embodiment of the disclosure. In FIG. 4, a similar case distribution diagram 42 shows how many similar case data there are, and the similar case data is presented in a form of a cost-effectiveness distribution diagram 421. There are multiple display points 422 in the cost-effectiveness distribution diagram 421, and each of the display points 422 is associated with the current cost and the healing speed of one similar case data.

In an embodiment, the similar case distribution diagram 42 may provide a filtering range 423 for the user to click on to adjust the number of the similar case data. The filtering range 423 may be, for example, a large range, a medium range, or a small range. Specifically, the user may first click on a target display point 422a, and then select "the small range" in the filtering range in the filtering condition 423. The processor 13 receives a selection command corresponding to the target display point 422a and a distribution range command corresponding to the filtering range. The part of the similar case data is filtered out based on the selection command and the distribution range command. That is, taking the target display point 422a in the cost-effectiveness distribution diagram 421 as the center, a radius size corresponding to "the small range" is captured, and a less part of the similar case data is displayed. Similarly, in response to "the large range" in the filtering range being selected in the filtering condition 423 by the user, the processor 13 captures a radius size corresponding to "the large range" and displays a greater part of the similar case data.

The processor 13 may summarize into multiple dressing types 424 corresponding to the part of the similar case data according to the part of the similar case data, display each of the dressing types 424 in the cost-effectiveness distribution diagram 421, and present a ratio of each of the dressing types 424 in the form of a pie chart 425, for example. The user may know which dressing types and proportions thereof have been used in the part of the similar cases relative to the wound status of the wound 312 in FIG. 3A though the pie chart 425.

In step 251, average recovery days, average recovery cost, and recovery cost standard deviation corresponding to at least one dressing item in each of the dressing types according to at least part of the similar case data associated with each of the dressing types are calculated by the processor 13.

For example, the user may click on the dressing type "hydrophilic fiber dressing" which the user wants to further view on the pie chart 425 in FIG. 4. The processor 13 calculates the average recovery days, the average recovery cost, and the recovery cost standard deviation corresponding to the dressing types in "the hydrophilic fiber dressing" according to the similar case data associated with "the hydrophilic fiber dressing".

In step S252, a dressing usage result is generated by the processor 13 according to the average recover days, the average recovery cost, and the recovery cost standard deviation corresponding to at least one dressing type in each of the dressing types.

At the same time, in step S261, multiple keywords are searched from the at least part of the similar case data associated with each of the dressing types by the processor 13. Specifically, the processor 13 searches for the keywords from a related item (for example: skin and wound cleaning, wound debridement, referral to specialists, infection and preventive control, skin protection, skin care, stress reduction, attention to dressing changes, life note) in accordance with care methods in a health education text of the at least part of the similar case data associated with each of the dressing types. In step S262, a care method text and a life note text are generated by the processor 13 from the multiple keywords through a Generative Pre-training Transformer (GPT) process.

In step S270, the dressing usage result, the care method text, and the life note text generated by the processor 13 are displayed on the display 14.

Figure 5A:
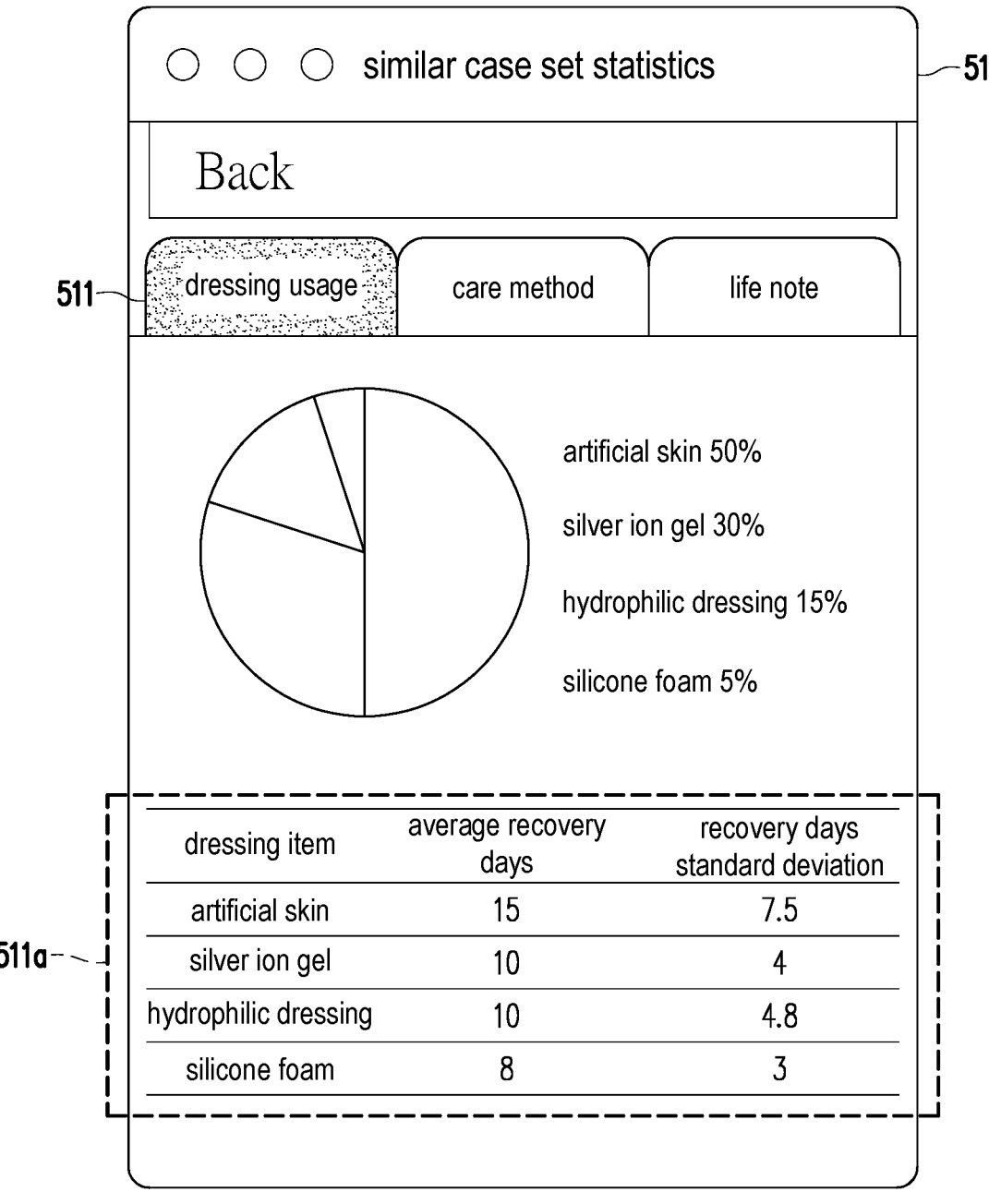
FIGS. 5A to 5C are schematic diagrams of similar case set statistics in a care plan recommendation method according to an embodiment of the disclosure.
Figure 5B:
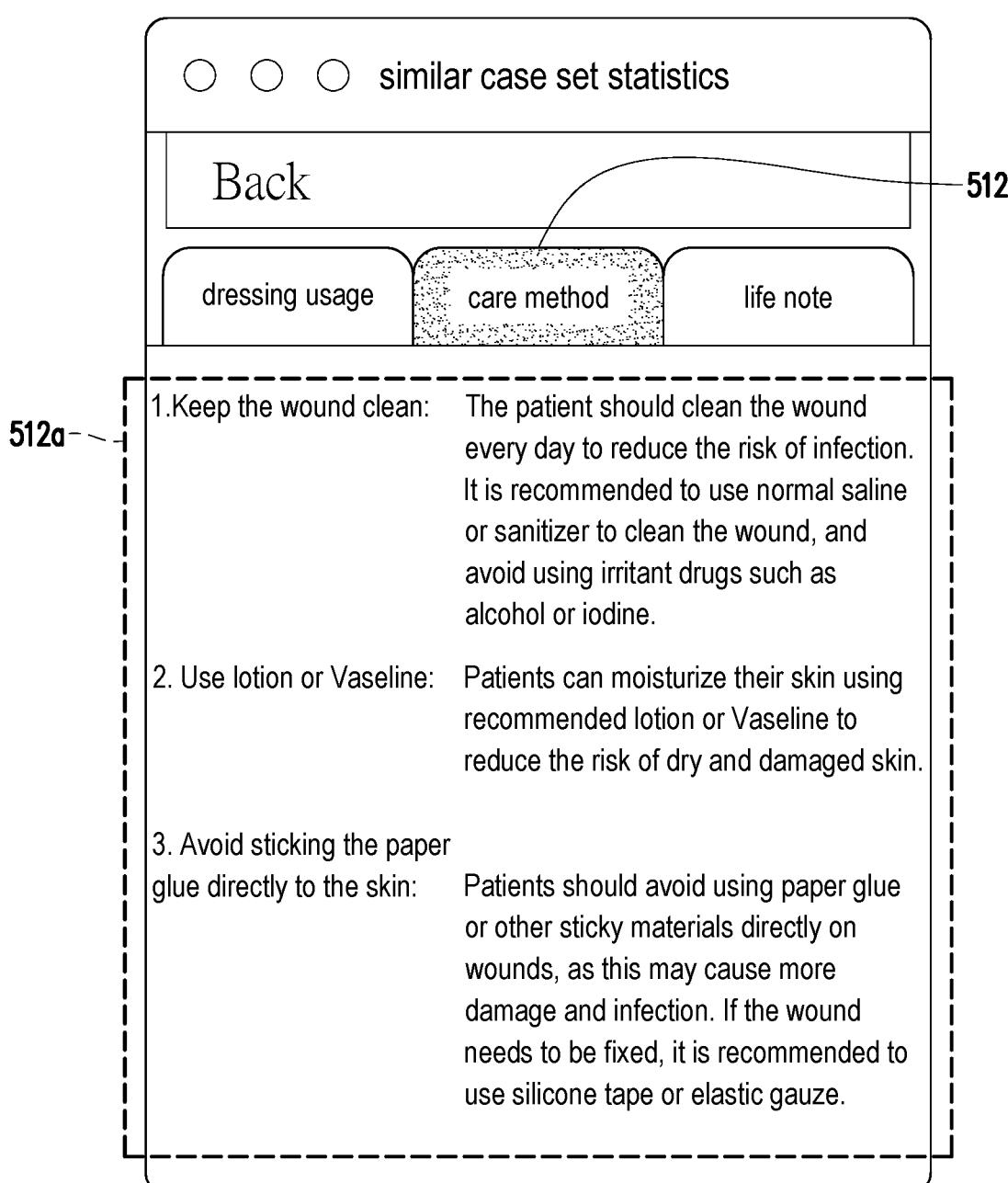
Figure 5C:
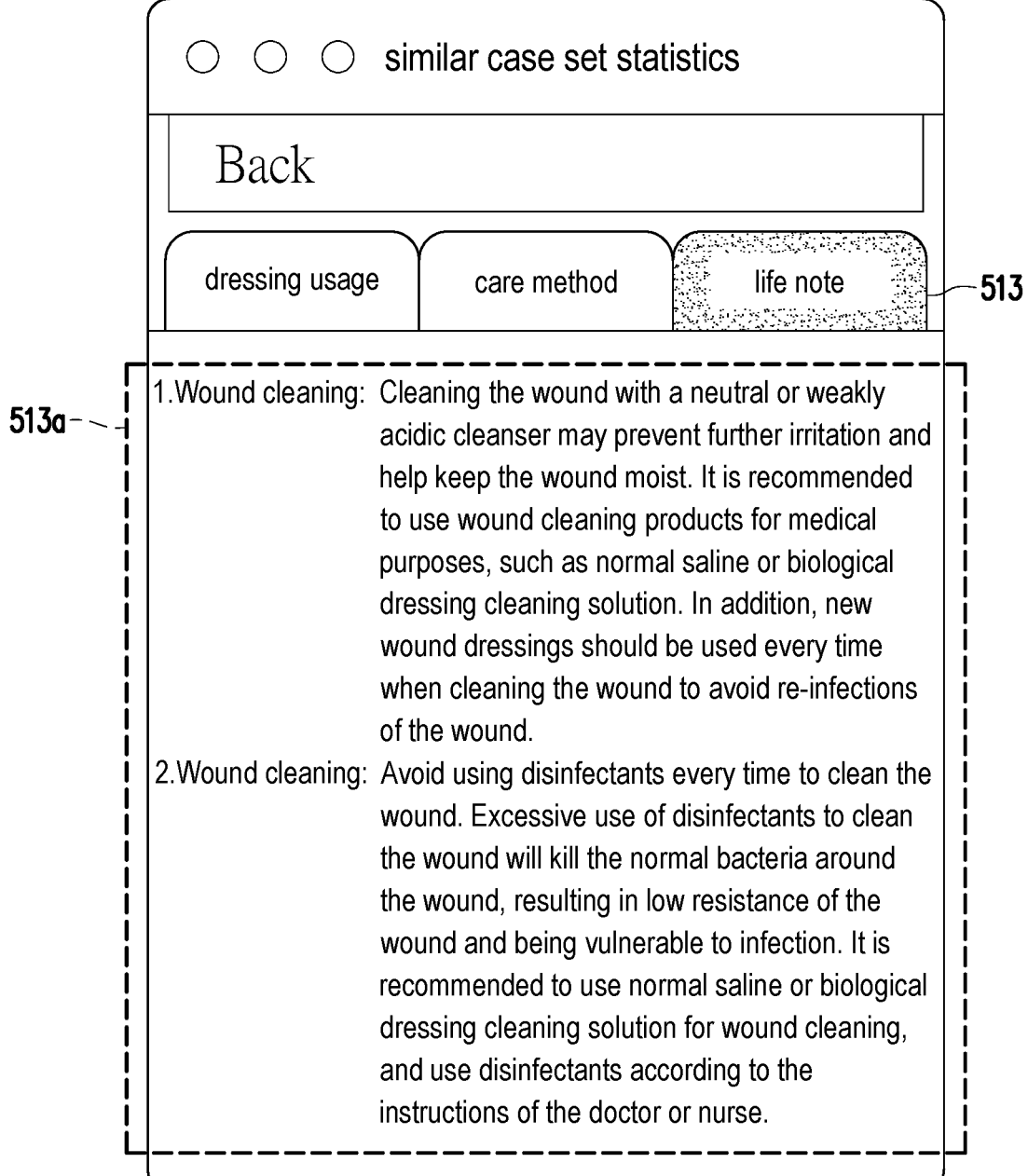

FIGS. 5A to 5C are schematic diagrams of similar case set statistics 51 in a care plan recommendation method 2 according to an embodiment of the disclosure. The similar case set statistics 51 include three pages, namely a "dressing usage" page 511, a "care method" page 512, and the "life note" page 513. The "dressing usage" page 511, the "care method" page 512, and the "life note" page 513 are all information provided for reference by users (for example, wound experts, nurses, home caregivers).

The example in FIGS. 5A to 5C is that after the user clicks on "the hydrophilic fiber dressing" on the pie chart 425 in FIG. 4, the dressing usage result, the care method text, and the life note text generated by the processor 13 through the steps S251, S252, S261, and S262 according to "the hydrophilic fiber dressing" are displayed on the similar case set statistics 51 by the display 14 as the dressing usage result shown in FIG. 5A, the care method text shown in FIG. 5B, and the life note text shown in FIG. 5C. Please refer to FIGS. 5A to 5C at the same time.

A dressing usage result 511*a* on the "dressing usage" page 511 displays the corresponding average recovery days and a recovery days standard deviation for each of "artificial skin", "silver ion gel", "hydrophilic dressing", and "silicone foam" in "the hydrophilic fiber dressing". The "dressing usage" page 511 may also display the corresponding average recovery cost (not shown) and the recovery cost standard deviation (not shown) for each of "the artificial skin", "the silver ion gel", "the hydrophilic dressing", and "the silicon foam" in "the hydrophilic fiber dressing".

The "care methods" page 512 displays a care method text 512*a* generated through the GPT process using the keywords related to "the hydrophilic fiber dressing". The "life note" page 513 displays a life note text 513*a* generated through the GPT process using the multiple keywords related to "the hydrophilic fiber dressing".

Based on the above, the care plan recommendation system and care plan recommendation method of the disclosure propose a method tool for exploring disease conditions and recommending care plans using the similar cases, aiming to help medical personnel effectively record, manage, and care for wounds. The care plan recommendation system and the care plan recommendation method described in the disclosure may provide detailed records of target wounds, extract relevant fields as needed, support diversified queries, generate cost-effectiveness analysis, and provide intelligent care method suggestions and dressing selection, hoping to improve the optimization of a care process when the front-end nursing personnel facing complex wounds. Moreover, the care plan recommendation system and the care plan recommendation method of the disclosure simplify a wound management process, improve work efficiency, ensure that the patients receive high-quality care, and help optimize the allocation of medical resources.

What is claimed is:

1. A care plan recommendation system, comprising:
   a storage device, configured to store a plurality of wound case data;
   an image capturing device, configured to captured a wound image of a wound; and
   a processor, coupled to the image capturing device and the storage device, configured to execute:
   analyzing a wound status of the wound according to the wound image;
   filtering out a plurality of similar case data from the plurality of wound case data based on at least one filtering condition according to the wound status;
   summarizing into a plurality of dressing types according to a part of the similar case data in the plurality of similar case data;
   calculating average recovery days, average recovery cost, and recovery cost standard deviation corresponding to at least one dressing item in each of the plurality of dressing types according to at least part of the similar case data associated with each of the plurality of dressing types, and generating a dressing usage result; and
   searching for a plurality of keywords from the at least part of the similar case data associated with each of the plurality of dressing types, and converting the plurality of keywords to generate a care method text and a life note text through a Generative Pre-training Transformer (GPT) process; and
   a display, coupled to the processor and configured to display the dressing usage result, the care method text, and the life note text.

2. The care plan recommendation system according to claim 1, wherein the wound status comprises a numerical record and a text record.

3. The care plan recommendation system according to claim 1, wherein the processor is further configured to convert the plurality of wound case data into an intersection matrix based on the at least one wound condition according to the wound status, filter out the plurality of similar case data based on the intersection matrix, and generate a cost-effectiveness distribution diagram based on the plurality of similar case data.

4. The care plan recommendation system according to claim 3, wherein the cost-effectiveness distribution diagram comprises a plurality of display points, and each of the plurality of display points is associated with a current cost and a healing speed of each of the plurality of similar case data.

5. The care plan recommendation system according to claim 4, wherein the processor is further configured to receive a selection command and a distribution range command corresponding to one of the plurality of display points, and filter out the part of the similar case data based on the selection command and the distribution range command.

6. The care plan recommendation system according to claim 1, wherein the processor is further configured to search for a plurality of keywords according to a health education text of the at least part of the similar case data associated with each of the plurality of dressing types.

7. A care plan recommendation method, comprising:

capturing a wound image of a wound;

analyzing a wound status of the wound according to the wound image;

filtering out a plurality of similar case data from a plurality of wound case data based on at least one filtering condition according to the wound status;

summarizing into a plurality of dressing types according to a part of the similar case data in the plurality of similar case data;

calculating average recovery days, average recovery cost, and recovery cost standard deviation corresponding to at least one dressing item in each of the plurality of dressing types according to the at least part of the similar case data associated with each of the plurality of dressing types, and generating a dressing usage result;

searching for a plurality of keywords from the at least part of the similar case data associated with each of the plurality of dressing types, and converting the plurality of keywords to generate a care method text and a life note text through a Generative Pre-training Transformer (GPT) process; and displaying the dressing usage result, the care method text, and the life note text.

8. The care plan recommendation method according to claim 7, wherein the wound status comprises a numerical record and a text record.

9. The care plan recommendation method according to claim 7, further comprising:

converting the plurality of wound case data into an intersection matrix based on the at least one filtering condition according to the wound status, filtering out the plurality of similar case data based on the intersection matrix, and generating a cost-effectiveness distribution diagram based on the plurality of similar case data.

10. The care plan recommendation method according to claim 9, wherein the cost-effectiveness distribution diagram comprises a plurality of display points, and each of the plurality of display points is associated with a current cost and a healing speed of each of the plurality of similar case data.

11. The care plan recommendation method according to claim 10, further comprising:

receiving a selection command and a distribution range command corresponding to one of the plurality of display points, and filtering out the part of the similar case data based on the selection command and the distribution range command.

12. The care plan recommendation method according to claim 7, further comprising:

searching for a plurality of keywords according to a health education text in the at least part of the similar case data associated with each of the plurality of dressing types.

* * * * *